(12) United States Patent
Mulholland

(10) Patent No.: US 8,103,355 B2
(45) Date of Patent: Jan. 24, 2012

(54) METHOD AND DEVICE FOR MINIMALLY INVASIVE SKIN AND FAT TREATMENT

(75) Inventor: R. Stephen Mulholland, Toronto (CA)

(73) Assignee: Invasix Ltd, Yokneam (IL)

(*) Notice: Subject to any disclaimer, the term of this patent is extended or adjusted under 35 U.S.C. 154(b) by 1225 days.

(21) Appl. No.: 11/879,116

(22) Filed: Jul. 16, 2007

(65) Prior Publication Data

US 2009/0024192 A1 Jan. 22, 2009

(51) Int. Cl.
*A61B 18/04* (2006.01)
*A61B 18/08* (2006.01)

(52) U.S. Cl. ............... 607/101; 607/100; 606/9; 606/28

(58) Field of Classification Search .................. 607/100, 607/101; 606/28, 33
See application file for complete search history.

(56) References Cited

U.S. PATENT DOCUMENTS

| | | | |
|---|---|---|---|
| 4,985,027 A | 1/1991 | Dressel | 606/15 |
| 5,102,410 A | 4/1992 | Dressel | 606/15 |
| 5,123,903 A | 6/1992 | Quaid et al. | 604/22 |
| 5,143,063 A | 9/1992 | Fellner | 601/3 |
| 5,458,596 A * | 10/1995 | Lax et al. | 606/31 |
| 5,660,836 A | 8/1997 | Knowlton | 424/400 |
| 5,755,753 A | 5/1998 | Knowlton | 607/98 |
| 5,871,524 A | 2/1999 | Knowlton | 607/101 |
| 5,919,219 A | 7/1999 | Knowlton | 607/102 |
| 5,948,011 A | 9/1999 | Knowlton | 607/101 |
| 6,047,215 A | 4/2000 | McClure et al. | 607/101 |
| 6,241,753 B1 | 6/2001 | Knowlton | 607/101 |
| 6,273,884 B1 | 8/2001 | Altshuler et al. | 606/9 |
| 6,277,116 B1 * | 8/2001 | Utely et al. | 606/42 |
| 6,311,090 B1 | 10/2001 | Knowlton | 607/101 |
| 6,346,107 B1 | 2/2002 | Cucin | |
| 6,354,297 B1 * | 3/2002 | Eiseman | 128/898 |
| 6,377,854 B1 | 4/2002 | Knowlton | 607/101 |
| 6,377,855 B1 | 4/2002 | Knowlton | 607/101 |
| 6,378,380 B1 | 4/2002 | Kusters et al. | 73/861.63 |
| 6,381,497 B1 | 4/2002 | Knowlton | 607/101 |
| 6,381,498 B1 | 4/2002 | Knowlton | 607/101 |
| 6,394,973 B1 | 5/2002 | Cucin | |
| 6,405,090 B1 | 6/2002 | Knowlton | 607/102 |
| 6,425,912 B1 | 7/2002 | Knowlton | 607/101 |
| 6,430,446 B1 | 8/2002 | Knowlton | 607/101 |
| 6,438,424 B1 | 8/2002 | Knowlton | 607/101 |
| 6,453,202 B1 | 9/2002 | Knowlton | 607/102 |
| 6,461,378 B1 | 10/2002 | Knowlton | 607/104 |
| 6,470,216 B1 | 10/2002 | Knowlton | 607/101 |

(Continued)

FOREIGN PATENT DOCUMENTS

WO WO 03/079916 10/2003

(Continued)

*Primary Examiner* — Roy Gibson
*Assistant Examiner* — Kaitlyn Smith
(74) *Attorney, Agent, or Firm* — Ohlandt, Greeley, Ruggiero & Perle, L.L.P.

(57) ABSTRACT

A RF electrode for use in a device for thermal fat destruction and skin tightening is provided. The RF electrode comprises a handle, a cannula shaft that extends from the handle and in turn comprises a dielectric material. The shaft is insertable inside a body at a treatment area. The shaft also comprises an electrode tip that is positioned on the cannula at a location distal to the handle. The electrode tip comprises a RF conductive material. A device for thermal fat destruction and skin tightening and method therefore are also provided.

13 Claims, 6 Drawing Sheets

U.S. PATENT DOCUMENTS

| | | |
|---|---|---|
| 6,652,522 B2 | 11/2003 | Cucin |
| 6,662,054 B2 | 12/2003 | Kreindel et al. .............. 607/101 |
| 6,749,626 B1 | 6/2004 | Bhat et al. ...................... 623/1.1 |
| 6,761,701 B2 | 7/2004 | Cucin |
| 6,872,199 B2 | 3/2005 | Cucin |
| 7,112,200 B2 | 9/2006 | Cucin ............................. 606/49 |
| 7,736,357 B2 * | 6/2010 | Lee et al. ........................ 606/34 |
| 2002/0188280 A1 | 12/2002 | Nguyen et al. |
| 2003/0055471 A1 * | 3/2003 | Fenn et al. .................... 607/101 |
| 2003/0153960 A1 * | 8/2003 | Chornenky et al. ............. 607/72 |
| 2004/0019371 A1 * | 1/2004 | Jaafar et al. ..................... 607/50 |
| 2005/0055073 A1 * | 3/2005 | Weber ............................. 607/99 |
| 2006/0036300 A1 | 2/2006 | Kreindel |
| 2007/0060989 A1 * | 3/2007 | Deem et al. ..................... 607/99 |
| 2009/0043247 A1 * | 2/2009 | Kreindel et al. ................ 604/21 |

FOREIGN PATENT DOCUMENTS

| | | |
|---|---|---|
| WO | WO 03/103768 | 12/2003 |

* cited by examiner

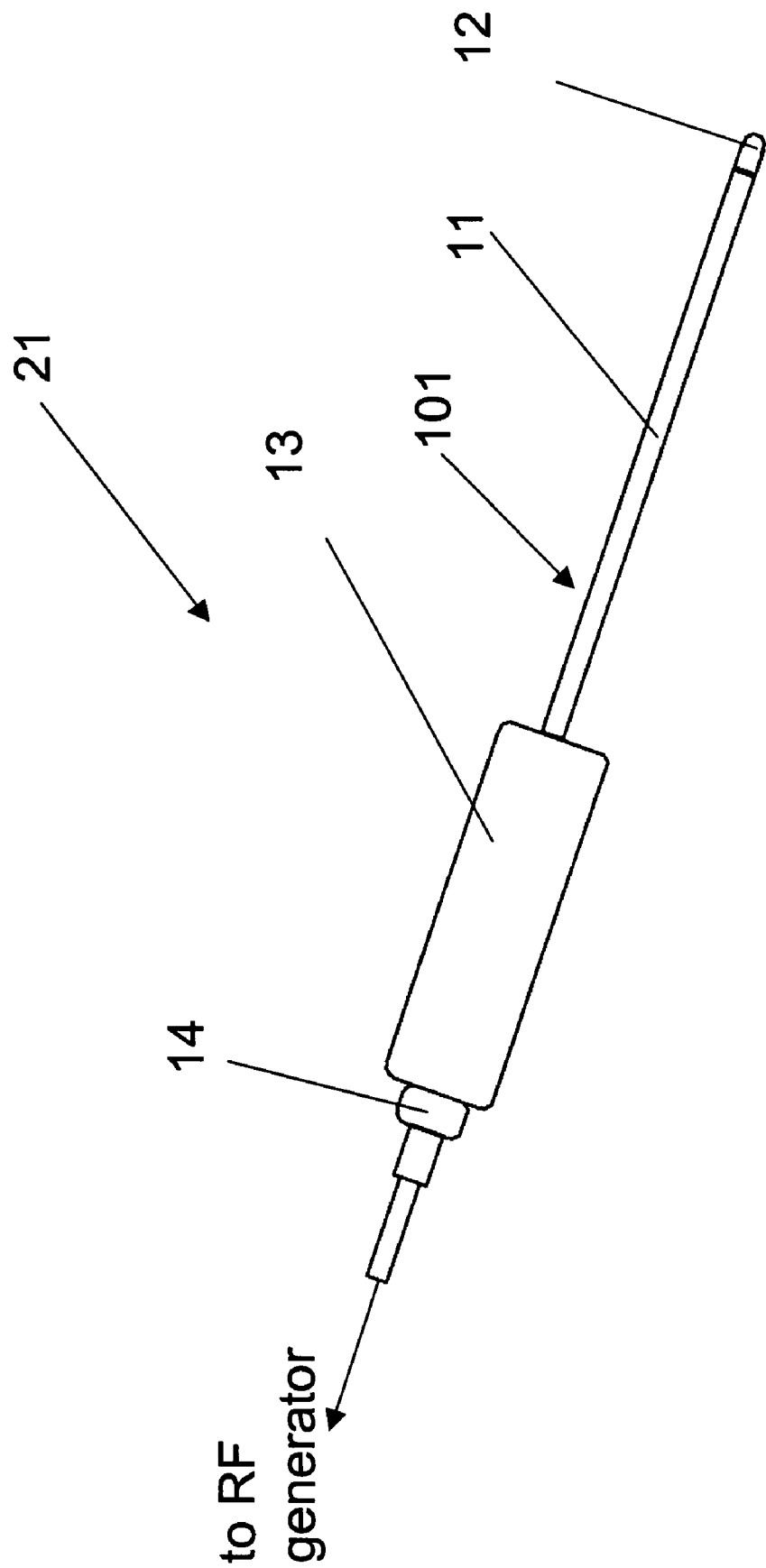

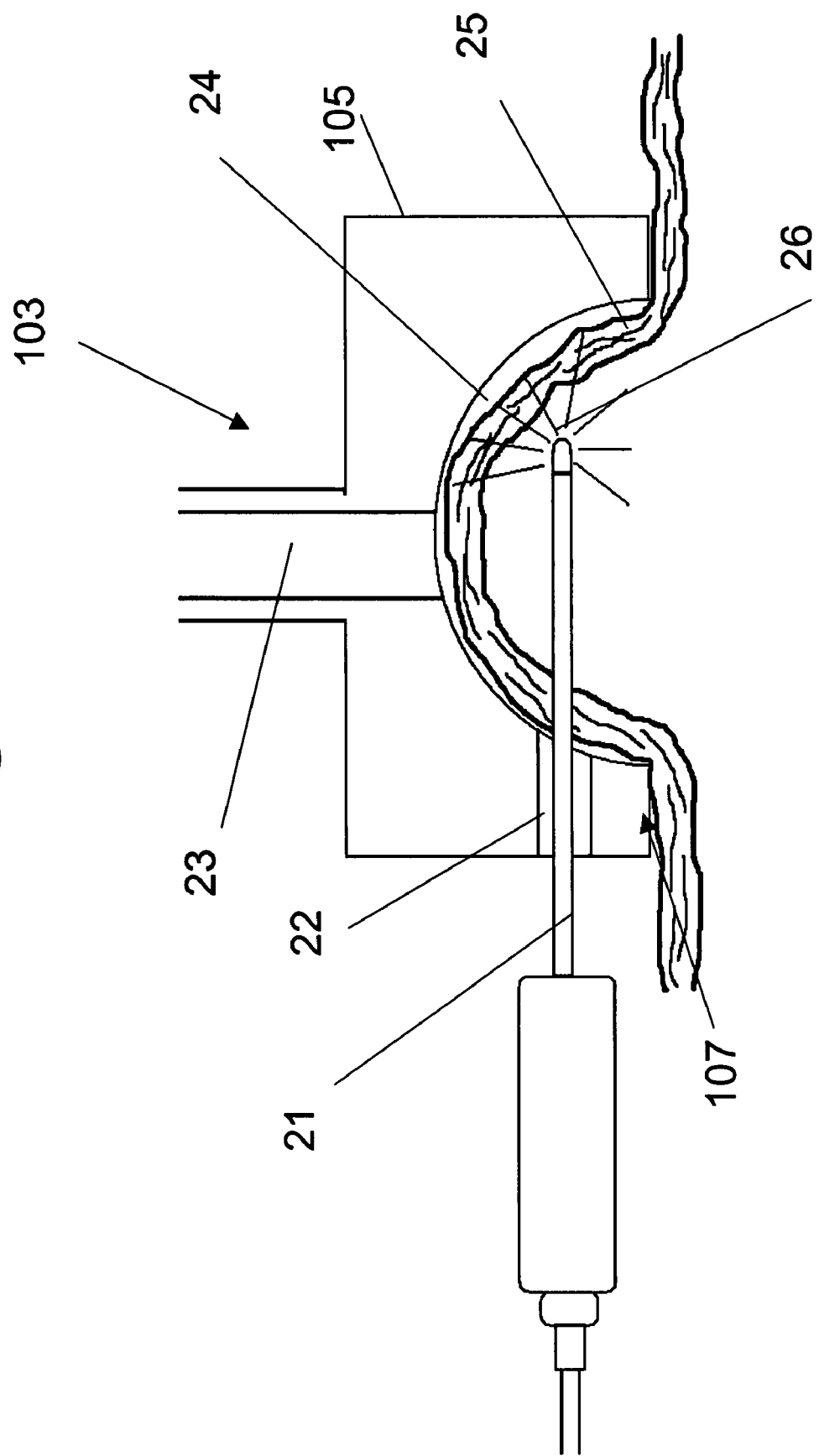

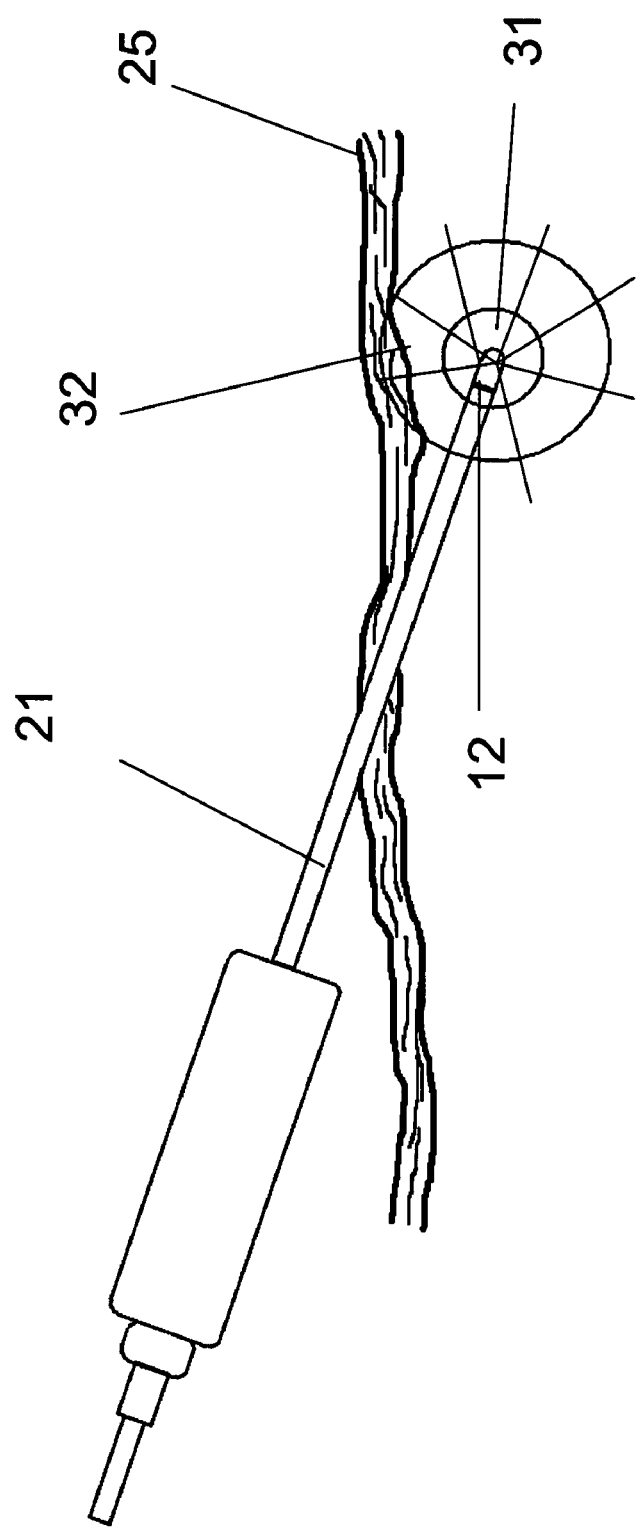

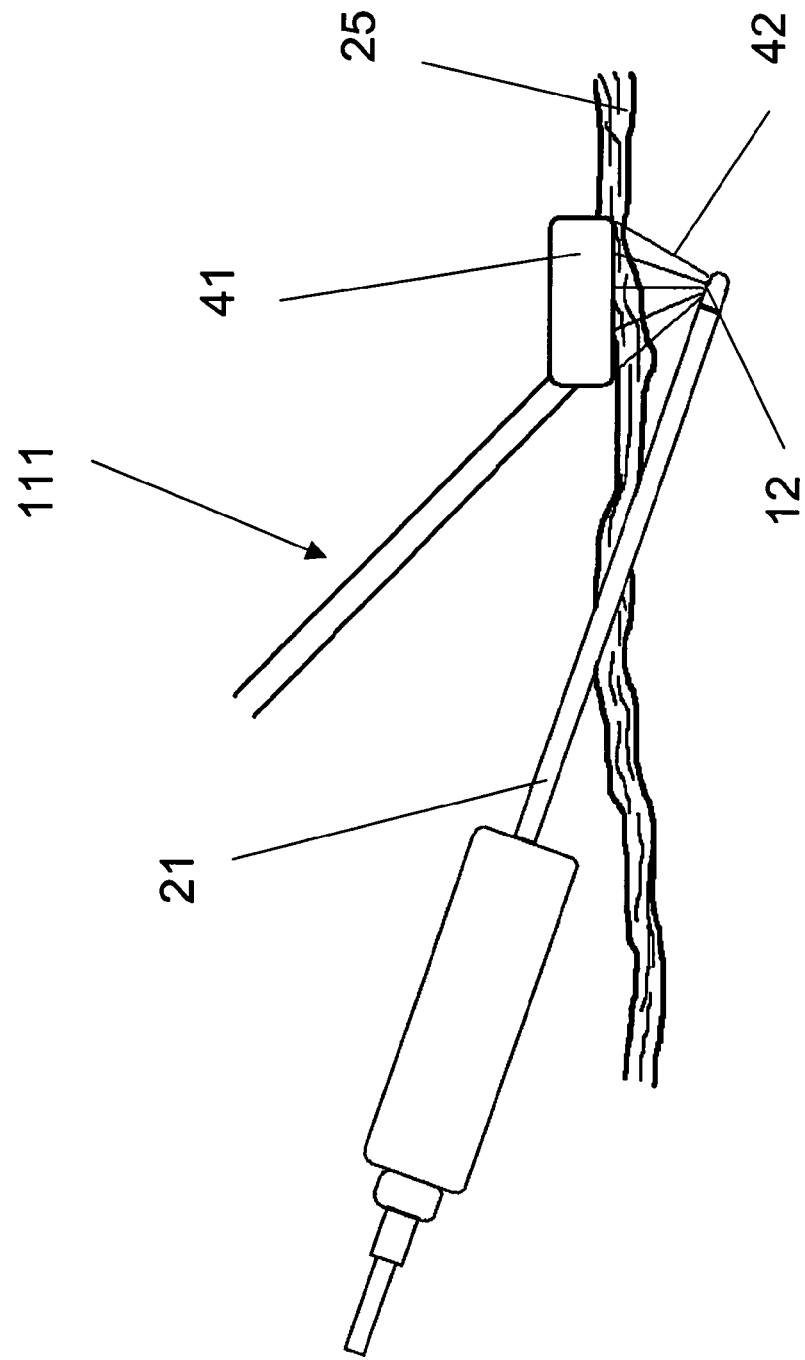

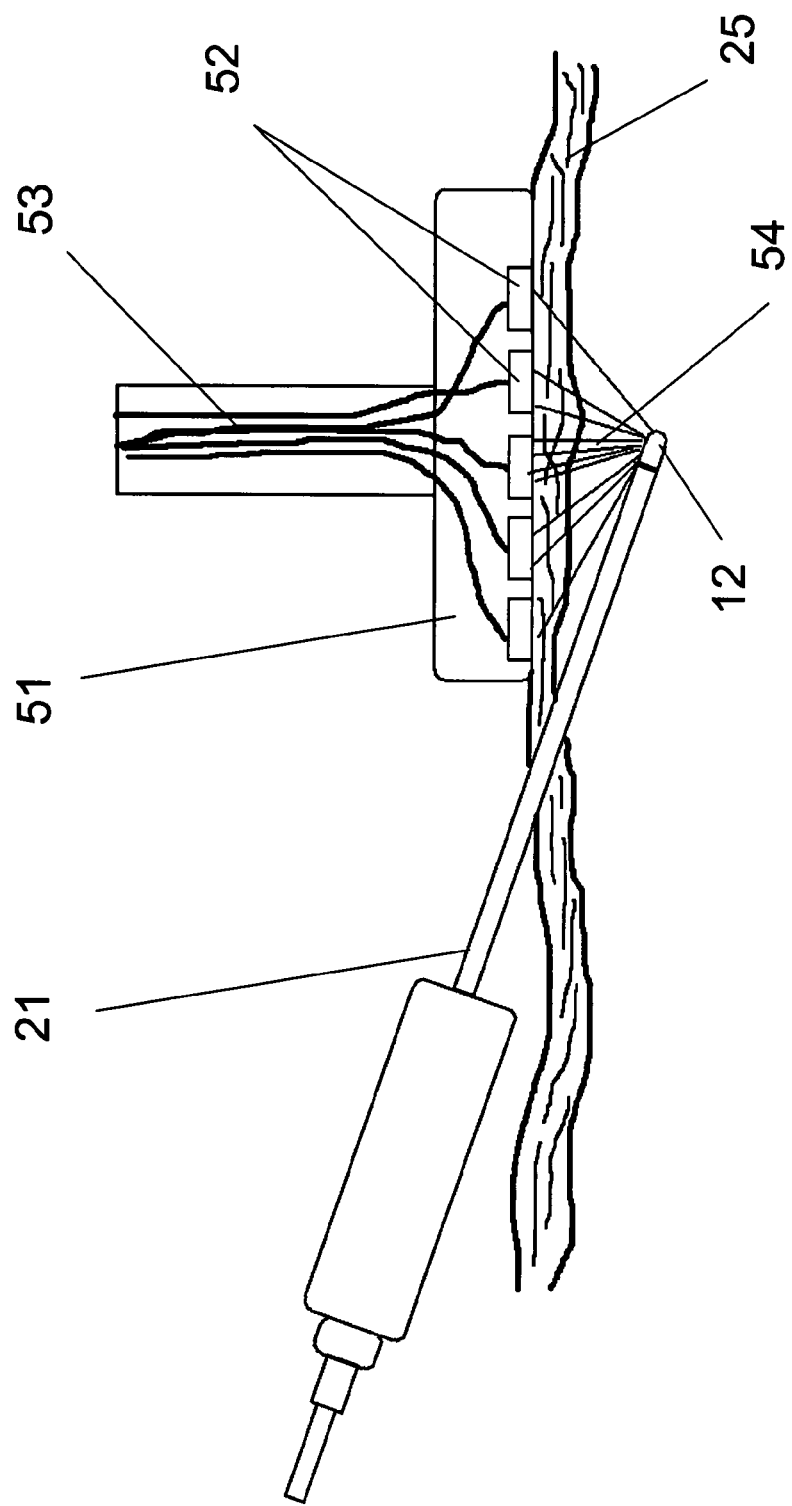

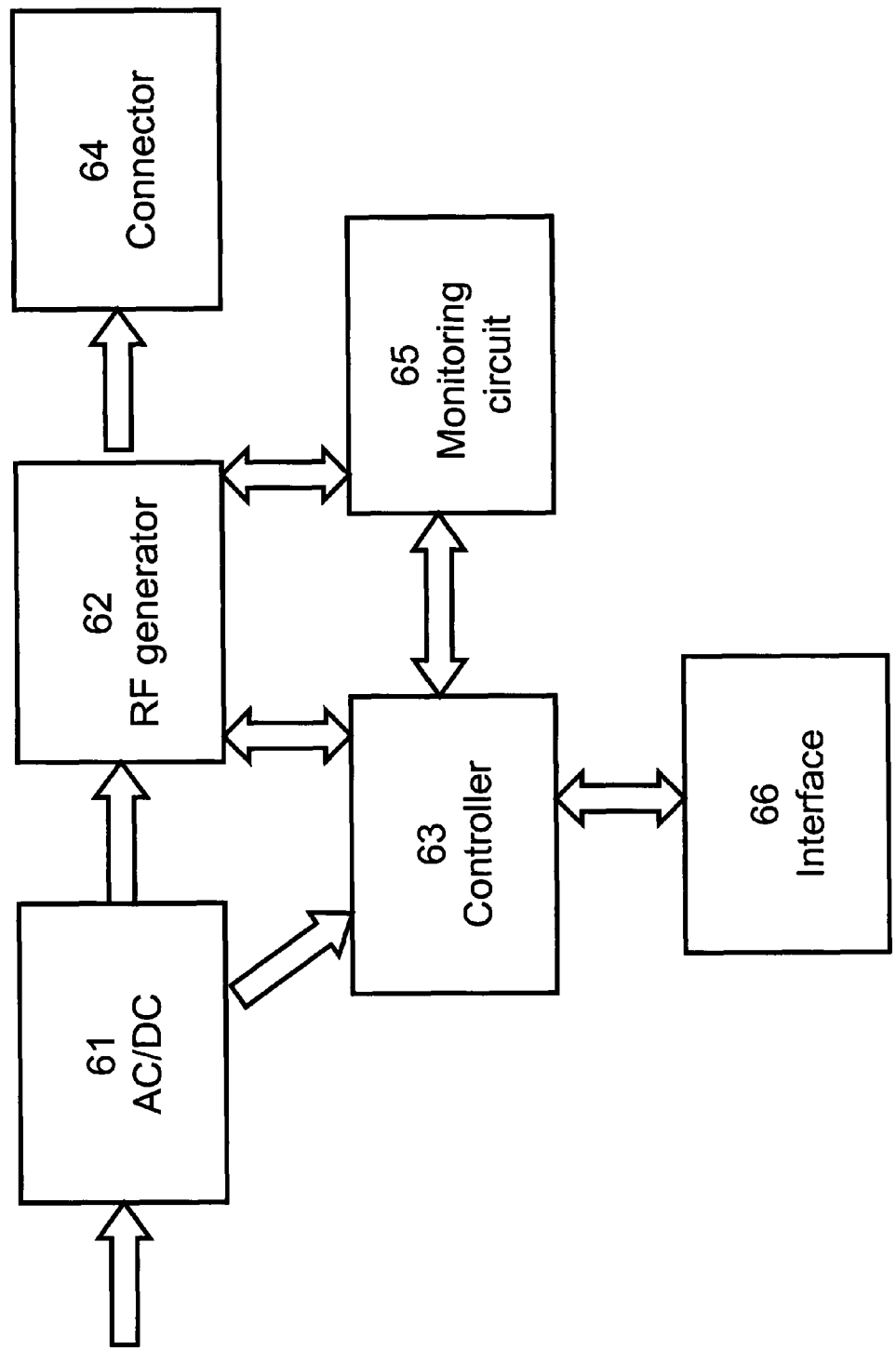

METHOD AND DEVICE FOR MINIMALLY INVASIVE SKIN AND FAT TREATMENT

FIELD OF THE INVENTION

The invention relates to a method and device for skin tightening and fat destruction.

BACKGROUND OF THE INVENTION

Liposuction remains the number one cosmetic surgery procedure in North America. Liposuction is performed by inserted fenestrated cannulas into fat. The fat is removed under vacuum pressure through the fenestrated openings in the cannula. Fat may also be destroyed by ultrasonic probes inserted directly into the fat causing cavitration or by using a reciprocating probe inserted into the fat.

Skin tissue consists of an outer epidermal layer overlying a dermal layer that is in contact with a layer of subcutaneous adipose tissue. Excess adipose tissue is responsible for such medical problems as obesity, cellulites, loose skin, and wrinkles.

Localized collections of excess fat, focal lipodystrophies, result in convex skin distension and undesirable skin contours. By destroying the adipose cells, the appearance of the outer layer of the skin can be improved and the convex distenstions reduced and the contours improved. The destroyed adipose tissue is evacuated from the body by the lymphatic system. The destruction of adipose tissue in the sub-dermal layer often results in weight reduction, cellulite reduction, loose skin reduction, deep wrinkle reduction and body re-contouring. Reduction of fat in subcutaneous layer can also create loose skin that should be tightened to create an aesthetically pleasing skin appearance.

Most existing wrinkle treatment methods target the collagen but do not have a significant effect on deep wrinkles or the underlying adipose tissue. Radio frequency (RF) energy has been actively used for the treatment of epidermal and dermal layers of the skin. For example, U.S. Pat. No. 6,749,626 describes the use of RF energy for collagen formation in the dermis. U.S. Pat. No. 6,241,753 describes a method for collagen scar formation. U.S. Pat. Nos. 6,470,216, 6,438,424, 6,430,446 and 6,461,378 disclose a method and apparatus for destroying the collagen matrix using RF, cooling and a special electrode structure that smoothes the skin surface. U.S. Pat. Nos. 6,453,202, 6,405,090, 6,381,497, 6,311,090, 5,871,524 and 6,425,912 describe a method and apparatus for delivering RF energy to the skin using membrane structure. U.S. Pat. Nos. 6,453,202 and 6,425,912 describe a method and apparatus for delivering RF energy to the skin using dielectric electrodes. U.S. Pat. Nos. 6,381,498, 6,377,855, 5,919,219, 5,948,011, 5,755,753 describe a method of collagen contraction using RF energy, and a reverse temperature gradient on the skin surface.

U.S. Pat. Nos. 6,378,380, 6,377,854 and 5,660,836 describe a method of liposculpturing using RF energy and external cooling to affect the collagen inside the adipose tissue.

Another method to reduce and redistribute adipose issue is skin massaging. This method is based on improving of blood circulation and increasing fat metabolism. U.S. Pat. No. 6,662,054 describes a method for skin massaging in combination with non-aggressive RF heating for increasing skin and fat metabolism.

U.S. Pat. No. 6,273,884 to Altshuler et al. discloses simultaneous application of optical energy and negative pressure to the skin in order to treat a skin defect. This method is limited by the light penetration depth, which does not exceed a 1-2 millimetres.

U.S. Pat. No. 5,143,063 describes a method based on thermal destruction of fat using the focusing of microwave or ultrasound energy in adipose tissue. But both types of energy are very expensive and its safety limitations are not clear.

A popular current trend in minimally invasive adipose destruction involves the injection of lipochaltic compounds, principally deoxycholate and phosphatidyl choline, directly into the adipose tissue, where the chemicals destroy the adipocyte cell membrane.

The above mentioned methods attempt to solve the problems created by localized excesses of adipose tissue such as body contouring, loose skin, and deep wrinkles, by contracting the superficial collagen tissue or directly altering the fate cell. These methods are limited in their penetration depth and by the degree of deep fat contouring that can be achieved by modest tightening of the skin.

Another popular method for reduction of adipose tissue is liposuction. This method combines mechanical destruction of fat with removing the fat debris using aspirating system. Disadvantage of this method is that mechanical action destroying the fat also damages the blood vessels, nerves and connective tissue. The other problem of liposuction procedure is loose skin appeared on the treated area after the fat reduction. U.S. Pat. No. 5,123,903 describes a device where tissue aspiration is assisted by ultrasound energy. Using of ultrasound energy helps to break up adipose tissue and improves its aspiration.

U.S. Pat. Nos. 4,985,027 and 5,102,410 describes a device and method for soft tissue aspiration using probe delivering laser energy inside the tissue for better tissue cutting and blood vessel coagulation.

U.S. Pat. Nos. 7,112,200, 6,346,107, 6,394,973, 6,652,522, 6,761,701, 6,872,199 describe an electro cauterizing cannula for liposuction were RF energy used for reduction of bleeding and tissue coagulation to improve the aspiration.

U.S. Pat. No. 6,047,215 describes a device were two RF antennas are applied to the skin surface and directed to the same area inside the adipose tissue to create higher energy density inside the body than on the surface.

There remains a need for a method and device that addresses at least one of the above-presented shortcomings.

SUMMARY OF THE INVENTION

A RF electrode for use in a device for thermal fat destruction and skin tightening is provided. The RF electrode comprises a handle, a cannula shaft that extends from the handle and in turn comprises a dielectric material. The shaft is insertable inside a body at a treatment area. The shaft also comprises an electrode tip that is positioned on the cannula at a location distal to the handle. The electrode tip comprises a RF conductive material.

A device for thermal fat destruction and skin tightening is provided. The device comprises an internal RF electrode in turn comprising a handle, a cannula shaft that extends from the handle and in turn comprises a dielectric material. The shaft is insertable inside a body at a treatment area. The shaft also comprises an electrode tip that is positioned on the cannula at a location distal to the handle. The electrode tip comprises a RF conductive material.

The device also comprises an external electrode comprising a RF conductive element. The RF element of the external electrode is positionable on a skin surface above the treatment area of the internal electrode and has a larger conductive area than the internal electrode.

The device also comprises a RF generator that is connected to the internal and external electrodes. The RF generator delivers RF energy to the internal electrode at the level sufficient to destroy adipose tissue in vicinity of the electrode tip and RF energy to the external electrode at a level sufficient to heat the skin below second electrode to a sub-necrotic level.

The RF current generated is in the frequency range of 0.2 MHz to 100 MHz, preferably.

Alternately, a first alternate device for thermal fat destruction and skin tightening is provided. The device comprises an internal RF electrode in turn comprising a handle, a cannula shaft extending from the handle and in turn comprising a dielectric material. The shaft is insertable inside a body at a treatment area. The internal RF electrode also comprises an electrode tip that is positioned on the cannula at a location distal to the handle. The electrode tip comprises a RF conductive material.

The device also comprises an external electrode comprising a RF conductive element. The element is positionable on a skin surface above the treatment area of the internal electrode and has a fractional structure that comprises a plurality of conductive sub-elements. The skin contact dimensions of each sub-element measures up to 1 mm.

The device also comprises a RF generator that is connected to the internal and external electrodes. The RF generator delivers RF energy to the internal electrode at the level sufficient to destroy adipose tissue in vicinity of the electrode tip and RF energy to the external electrode at a level sufficient to create coagulation zones on the skin surface under the conductive sub-elements.

Preferably, the skin contact surface area of each conductive sub-element is less than 0.5 mm$^2$.

Preferably, the conductive sub-elements are needle shaped.

Alternately, a second alternate device for thermal fat destruction and skin tightening is provided. The alternate device comprises at least one internal RF electrode in turn comprising a handle, a cannula shaft extending from the handle and comprising a dielectric material (the shaft being insertable inside a body at a treatment area), and an electrode tip positioned on the cannula at a location distal to the handle. The electrode tip comprises a RF conductive material.

The device also comprises a skin protruder in turn comprising a body defining a cavity open to a surface of the protruder body, the cavity surface of the body being positionable on a skin surface above the treatment area of the internal electrode. The skin and associated underlying tissue can be drawn into the cavity to create a skin protrusion in response to a drawing force. The skin protruder further comprises an inlet for the RF electrode which allows the treatment of the tissue drawn into the cavity.

The device also comprises a RF generator that is connected to the RF electrode. The RF generator is configured to deliver RF energy to the RF electrode at the level sufficient to destroy adipose tissue in vicinity of the electrode tip.

The drawing force is vacuum negative pressure created within the cavity.

Alternately, a third device for thermal fat destruction and skin tightening is provided. The alternate device comprises at least one internal RF electrode in turn comprising a handle, a cannula shaft extending from the handle and comprising a dielectric material (the shaft being insertable inside a body at a treatment area), and an electrode tip positioned on the cannula at a location distal to the handle. The electrode tip comprises a RF conductive material.

The device also comprises an external electrode in turn comprising an electrode body. The electrode body is positionable on a skin surface above the treatment area of the internal electrode and has a plurality of conductive elements.

The device also comprises a RF generator connected to the internal and external electrodes, the RF generator for delivering RF energy to the internal electrode at the level sufficient to destroy adipose tissue in vicinity of the electrode tip and to the external electrode at a level sufficient to sufficient to heat the skin below second electrode to a sub-necrotic level.

The device also comprises a measuring system in communication with the electrodes and the RF generator for monitoring at least one electrical parameter of RF energy for each conductive element selected from the group consisting of current, voltage and impedance.

The measurements of electrical parameters are used for monitoring skin heating.

In its first method aspect, the invention provides a method of thermal fat destruction comprising, for each of one or more regions of body:
  deforming the skin so that the region of skin protrudes from surrounding skin;
  inserting one RF electrode in side the tissue in the protruded region;
  delivering RF energy to the electrodes so as to deliver sufficient RF energy to destroy adipose tissue in vicinity of internal electrode and create skin tightening near the external electrode;
  move internal electrodes inside the protruded skin surface to create uniform layer of damaged adipose tissue and uniform tightening of the skin.

In its second method aspect, the invention provides a method of thermal fat destruction and skin tightening comprising, for each of one or more regions of the skin:
  inserting RF electrodes into the tissue;
  positioning the electrode in the vicinity of skin surface;
  delivering RF energy to the electrode to damage the adipose tissue; and tighten the skin;
  move the electrode under the skin surface to create uniform layer of damaged adipose tissue and uniform tightening of the skin,
applying a quantity of RF energy sufficient to damage the adipose tissue.

In its third method aspect, the invention provides a method of thermal fat destruction and skin tightening comprising, for each of one or more regions of the skin:
  inserting RF electrodes into the tissue;
  applying second electrode to the skin surface above the internal electrode;
  delivering RF energy to the electrode to damage the adipose tissue; and tighten the skin;
  move both electrodes parallel the skin surface to create uniform layer of damaged adipose tissue and uniform tightening of the skin.

In its fourth method aspect, the invention provides a method of thermal fat destruction and skin tightening comprising, for each of one or more regions of skin:
  inserting RF electrodes into the tissue;
  applying a second structured electrode having independent conducted electrode to the skin surface above the internal electrode;
  delivering RF energy to the electrodes to damage the adipose tissue; and tighten the skin;
  move internal electrodes parallel the skin surface under the skin surface covered with structured external electrode to create uniform layer of damaged adipose tissue and uniform tightening of the skin.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows an internal RF electrode assembly in accordance with an embodiment;

FIG. 2 shows cavity with protruded skin and internal RF electrode delivering RF energy into the protruded skin volume in accordance with an embodiment;

FIG. 3 shows internal RF electrode positioned in vicinity of the skin surface to create heating of the skin and destruction of the fat around the electrode in accordance with an embodiment;

FIG. 4 shows RF electrode inserted into the skin and second electrode applied to the skin surface in accordance with an embodiment;

FIG. 5 shows structured external electrode applied to the skin surface and second electrode inserted into tissue in accordance with an embodiment; and FIG. 6 shows a system unit for operating RF electrodes in accordance with an embodiment.

DETAILED DESCRIPTION OF THE PREFERRED EMBODIMENTS

A method and device for adipose tissue destruction and simultaneous skin tightening while minimizing the mechanical damage to the skin and surrounding subcutaneous tissue is provided.

The device is based on a minimally invasive procedure where at least one electrode is inserted directly into the adipose tissue and radio-frequency energy is applied to the electrode tip.

The size of the electrode is designed to create higher energy density in the vicinity of the electrode. The RF energy density is high enough to create damage to the adipose tissue. Preferably, the applied RF energy is high enough to create adipocyte damage in the volume which is larger than electrode size. Destroying the tissue around internal electrode thereby minimizes needed mechanical action for the uniform destruction of adipose tissue.

The internal electrode may have one or more conductive areas with the same or different applied polarities of RF voltage.

The device may include an external electrode that may be applied to the skin surface. The size of external electrode and applied energy is adjusted to create skin tightening without thermal damage of the dermis and epidermis.

In one embodiment the internal electrode is a probe comprising a shaft having a lumen made from dielectric material and conductive metal tip connected to the end of the shaft is inserted into the body. The conductive tip is connected to the RF generator by conductor passing through the dielectric shaft. The probe has an electrical connector connected to the RF generator.

The external electrode has dielectric handle and electrically conductive member applied to the skin surface. The external electrode may have rounded edges for uniform skin heating or structured from plurality of small conductive elements for fractional skin treatment.

The internal and external electrodes can be connected mechanically to control distance between electrodes. Mechanical mechanism may have different predetermined positions fixing specific distances between electrodes. This mechanism provides control on treatment depth. Mechanical mechanism connecting two electrodes may have spring element to compress the skin between two electrodes.

The external electrode can be structured from a plurality of conductive elements. The conductive elements may have small enough area to create small coagulation zones on the skin surface. The optimal size of elements area contacting the skin to create skin coagulation is 50 microns to 300 microns. The area of coagulation zone preferably should not exceed 0.5 $mm^2$ to provide fast healing of the lesions.

In other embodiments each conductive element may have area larger than the tip of the internal electrode and creates skin collagen remodelling without any thermal damage to the skin. Structuring of the electrode provides opportunity for navigation of internal electrode by measuring electrical current through the elements of structured external electrode.

As will be understood, the parts of the electrodes coming in contact with the tissue should be made from biocompatible materials. For example, the internal electrode tip can be made from stainless steel or titan. RF electrodes may have thin dielectric coating providing capacitive electrical coupling.

The external electrode can be designed for smooth movement over the skin creating uniform effect in the skin and adipose tissue. A motion or position sensor can be imbedded into the one of electrode for controlling of electrode movement.

The parameters of the RF energy may be adjusted for destruction of adipose tissue and skin tightening. RF energy can be delivered in pulsed or continues mode. Frequency of RF current may vary from 200 KHz up to 100 MHz, the higher frequencies providing better coupling with skin surface. In order to improve electrical coupling the conductive solution can be applied to the skin surface. Conductive liquid or gel can be used to hydrate stratum corneum and improve electrical contact. RF energy can be controlled by the controlling of RF power. Alternately, the other option to control average RF power is delivering constant RF power with train of the pulses and control duty cycle of RF pulses.

Referring first to FIG. 1, an internal electrode assembly 21 is shown for applying RF energy inside the adipose tissue in accordance with one embodiment. The electrode assembly 21 is configured to be connected to an RF generator (not shown) via connector 14. The electrode assembly 21 is configured so that a portion of it can be inserted into the human body via an incision.

The internal RF electrode 21 comprises a handle 13, a cannula shaft 101 that extends from the handle 13 and in turn comprises a dielectric material. The shaft 101 is insertable inside a body at a treatment area. The shaft 101 also comprises an electrode tip 12 that is positioned on the cannula at a location distal to the handle 13. The electrode tip 12 comprises a RF conductive material. The shaft 101 has a diameter preferably in the range of 1 mm to 3 mm. Although, it will be apparent to those skilled in the art that the diameter selected may vary according to the dictates of the particular application or procedure.

The handle 13 is preferably designed for convenient use of the electrode 21 by an operator.

The internal electrode assembly 21 may be used as a component of a device for thermal fat destruction and skin tightening (not shown). In addition to the electrode 21, the device also comprises an external electrode (such as external electrode 111 illustrated in FIG. 4) which comprises a RF conductive element 41. The RF element 41 of the external electrode 111 is positionable on a skin surface above the treatment area of the internal electrode and has a larger conductive area than the internal electrode.

The device also comprises a RF generator (not shown) that is connected to the internal and external electrodes. The RF generator delivers RF energy to the internal electrode 21 at the level sufficient to destroy adipose tissue in vicinity of the electrode tip and RF energy to the external electrode at a level sufficient to heat the skin below second electrode to a sub-necrotic level.

The RF current generated is in the frequency range of 0.2 MHz to 100 MHz, preferably.

The internal electrode may be connected to the external electrode so as to maintain a predetermined distance between the electrode tip of the internal electrode and the conductive element of the external electrode.

The device may further comprise a spring mechanism that acts between the internal and external electrodes so as to urge the electrode tip of the internal electrode to contact the conductive element of the external electrode.

Referring to FIG. 2, an alternate device for thermal fat destruction and skin tightening is illustrated. The alternate device comprises at least one internal RF electrode 21 (as illustrated and described in relation to FIG. 1) in turn comprising a handle 13, a cannula shaft 101 extending from the handle 13 and comprising a dielectric material (the shaft 101 being insertable inside a body at a treatment area), and an electrode tip 12 positioned on the cannula 101 at a location distal to the handle 13. The electrode tip 12 comprises a RF conductive material.

The device also comprises a skin protruder 103 in turn comprising a body 105 defining a cavity 24 open to a surface 107 of the protruder body 105, the cavity surface 107 of the body 105 being positionable on a skin surface above the treatment area of the internal electrode 21. The skin and associated underlying tissue can be drawn into the cavity 24 to create a skin protrusion 25 in response to a drawing force. The skin protruder 103 further comprises an inlet 22 for the RF electrode 21 which allows the treatment of the tissue drawn into the cavity 24.

The device also comprises a RF generator that is connected to the RF electrode. The RF generator is configured to deliver RF energy 26 to the RF electrode at the level sufficient to destroy adipose tissue in vicinity of the electrode tip.

The drawing force is preferably negative pressure created within the cavity 24, such as from a vacuum (through outlet 23).

The drawing force may also be mechanical pressure created within the cavity 24.

The skin protruder 103 may additionally comprise a RF conductive element. In this operating configuration, the skin protruder 103 is connected to the RF generator. The RF generator is configured for delivering RF energy to the skin protruder 103 at a level sufficient to heat the drawn skin to a sub-necrotic level.

In other embodiment the RF assisted thermal fat destruction can be provided using mono-polar RF system having single treatment electrode which inserted into the adipose tissue. The return electrode can be used for closing electrical circuit or capacitive coupling to the ground can be used at RF frequency higher then 5 MHz Controlling the distance between electrode and skin surface it is possible to create fat damage in vicinity of electrode and heating of the collagen structure of the skin by diverging RF current. RF current may create necrotic or apoptotic damage to the fat. To create thermal effect in the dermis the depth of external electrode should not exceed 5 of its radius. For example, the internal electrode having diameter of 2 mm will provide heating of the skin if it located at the depth less than 5 mm.

The temperature required for the collagen remodelling depends on heating time. For short millisecond range pulses the required temperature is 50-60° C. If treatment time is a few minutes than temperature should be in the range 40-45° C. is required to cause collagen remodelling without skin damage.

In other embodiment the device may have circuit measuring tissue impedance. Change of measured impedance between electrodes may provide information about distance between electrodes. Measuring of the tissue impedance also provides information about skin heating and quality of electrical contact between external electrode and skin surface. Electronic circuit may measure RF current, voltage, impedance or other parameters. In the case of structured external electrode comprising plurality of conductive elements the measurements of the impedance between internal electrode and each conductive element provides accurate positioning of internal electrode. The tip of internal electrode is located under conductive element having higher electrical current. This navigation method may prevent delivering of excessive energy to the tissue.

Internal electrodes may have temperature sensors for measuring the temperature of the skin and adipose tissue.

Cooling of electrodes can be used to avoid damage of skin surface and sticking of coagulated adipose tissue to the internal electrode.

The system for powering and controlling RF energy delivery may comprise of a power supply that converts AC voltage from the wall plug to stabilized DC voltage. RF generator connected to the power supply and generating high frequency voltage. The RF generator may be designed to maintain constant power in the working range of parameters. System may have controller that control the RF parameters and user interface including LCD screen and touch screen. Controller may have microprocessor and dedicated software. Monitoring system is required to measure RF parameters including tissue impedance and/or RF current and/or RF voltage or other electronic parameters. System has connector to connect one or more electrodes to the system unit.

Referring to FIG. 3, the internal RF electrode 21 is shown positioned inside the body in vicinity of the skin 25 to create heating of the skin and destruction of the fat around the electrode. The RF energy density near the electrode tip 12 is higher and RF energy can be adjusted to create adipose tissue damage in the zone 31 around the tip 12. Due to divergence of electrical current the heating is decreased with the distance and in the peripheral zone 32 the created temperature will be below the damage threshold but still high enough to create skin 25 tightening.

Referring to FIG. 4, an alternate device for thermal fat destruction and skin tightening is illustrated. The alternate device comprises at least one internal RF electrode 21 (as illustrated and described in relation to FIG. 1) in turn comprising a handle 13, a cannula shaft 101 extending from the handle 13 and comprising a dielectric material (the shaft 101 being insertable inside a body at a treatment area), and an electrode tip 12 positioned on the cannula 101 at a location distal to the handle 12. The electrode tip 12 comprises a RF conductive material.

The device also comprises an external electrode 111 in turn comprising an electrode body 41. The electrode body 41 is positionable on a skin surface above the treatment area of the internal electrode 21. The RF element 41 of the external electrode 111 is positionable on a skin surface above the treatment area of the internal electrode and preferably has a larger conductive area than the internal electrode.

The device also comprises a RF generator (not shown) that is connected to the internal and external electrodes. The RF generator delivers RF energy to the internal electrode 21 at the level sufficient to destroy adipose tissue in vicinity of the electrode tip and RF energy to the external electrode at a level sufficient to heat the skin below second electrode to a sub-necrotic level.

In a preferred embodiment, the device also comprises a measuring system in communication with the electrodes (21 and 111) and the RF generator for monitoring at least one electrical parameter of RF energy for each conductive element selected from the group consisting of current, voltage and impedance. The measurements of electrical parameters are used for monitoring skin heating.

The conductive elements are preferably electrically insulated and/or grounded.

Referring to FIG. 5, an alternate device for thermal fat destruction and skin tightening is illustrated. The device comprises an internal RF electrode 21 (as illustrated and described in relation to FIG. 1) in turn comprising a handle 13, a cannula shaft 101 extending from the handle 13 and in turn comprising a dielectric material. The shaft 101 is insertable inside a body at a treatment area. The internal RF electrode 21 also comprises an electrode tip 12 that is positioned on the cannula 101 at a location distal to the handle 13. The electrode tip 12 comprises a RF conductive material.

The device also comprises an external electrode 51 comprising a RF conductive element. The element is positionable on a skin surface above the treatment area of the internal electrode 21 and has a fractional structure that comprises a plurality of conductive sub-elements 52. The skin contact dimensions of each sub-element 52 measures up to 1 mm. The stronger heating will be created near the small tip 12 of internal electrode and lower heating in the skin in vicinity of larger external electrode 41.

Preferably, the skin contact surface area of each conductive sub-element is less than 0.5 mm$^2$.

Preferably, the conductive sub-elements are needle shaped.

In a preferred embodiment, the external electrode is moveable over the skin surface.

The electrode 51 may alternately be characterised as comprising a plurality of electrically insulated conductive elements 52 applied to the skin. Each conductive element 52 is connected electrically to the RF generator via electrical harness 53. The highest electrical current 54 will be higher through the conductive element that is closer to the tip 12 of internal electrode 21.

Measuring electrical current through the each conductive element 52 the position of tip 12 can be determined.

The size of conductive element may be in the range of 3 mm for precise navigation up to 15 mm for treatment larger areas.

The device also comprises a RF generator that is connected to the internal and external electrodes. The RF generator delivers RF energy to the internal electrode at the level sufficient to destroy adipose tissue in vicinity of the electrode tip and RF energy to the external electrode at a level sufficient to create coagulation zones on the skin surface under the conductive sub-elements.

Referring to FIG. 6 a schematic view of a device unit for powering and controlling RF energy delivered through the RF electrodes is shown. The unit comprises power supply 61 for converting AC voltage to the stabilized DC voltage in the range of 12VDC to 300VDC. The RF generator 62 converts DC voltage supplied by the power supply 61 to high frequency voltage in the frequency range of 0.2 MHz to 100 MHz. The preferable frequency range is 0.5 MHz to 10 MHz. RF energy can be delivered in CW or pulse mode. Required average RF power depends on electrode geometry and may varied from 0.1 W up to 300 W. The preferable range of RF power is 0.5 W to 10 W. RF energy is delivered to the connector 64 of the unit. One or more RF electrodes may be connected to the unit connector 64. Controller circuit 63 is used to control output from RF generator. Controller 64 provides connection between user interface 66 and electronics inside the unit. Controller gets inputs from the RF monitoring circuit 65 and adjust output parameters according to the inputs. Monitoring circuit 65 measures electrical parameters of the skin and RF energy output. It can measure such parameters as RF voltage, RF current, skin impedance or conductivity. For example if measured impedance is too high indicating bad coupling of electrodes with the tissue controller 65 will stop RF energy delivery.

In use, the device described above in treating subcutaneous adipose tissue and tightening the skin, the following exemplary parameter values of RF energy may be used:
RF frequency: 0.2-100 MHz.
Average output power: from about 0.1 to about 300 W.
Delivered energy should create high enough temperature in the vicinity of electrode tip 12 to destroy adipose tissue. The temperature should exceed damage threshold of adipose tissue.

In connection with the device 10 and electrode described above, a method for thermal fat destruction and skin tightening is provided. The method comprises the steps of:
(a) inserting at least one RF electrode in adipose tissue under the skin surface;
(b) moving the RF electrode in relation to the skin surface at the distance from the surface that allows the RF current from the electrode to heat the skin.

In the method, the RF current used preferably has a frequency in the range of 0.2 MHz to 100 MHz. Additionally, the electrical parameters of the treated tissue are monitored during RF energy delivery.

During use, the RF current output to the RF electrode is preferably controlled by microcontroller circuit.

Alternately, the method for thermal fat destruction and skin tightening may be characterised as comprising the steps of:
(a) drawing the skin to create a protruded skin volume, a portion of which being adipose tissue;
(b) inserting at least one RF electrode into the adipose tissue inside protruded volume; and
(c) applying RF energy to the electrode sufficient to thermally destroy adipose tissue in vicinity of electrode.

As before, the RF energy is delivered at a frequency in the range of 0.2 MHz to 100 Hz, preferably, and, the electrical parameters of the adipose tissue are monitored during RF energy delivery.

The skin is drawn (thereby creating the protrusion) using negative pressure into a conductive cavity of a skin protruder.

Preferably, the conductive cavity is an external RF electrode.

Alternately, the method for thermal fat destruction and skin tightening may be characterized as comprising the steps of:
(a) inserting an internal RF electrode into adipose tissue under the skin surface;
(b) positioning an external RF electrode on the skin surface above the first electrode; and
(c) applying RF voltage to the electrodes sufficient to create thermal destruction of adipose tissue in vicinity of the internal electrode and sufficient to heat the skin up to sub-necrotic temperature in vicinity of external electrode.

The distance between internal and external electrodes may be controlled.

Any one of the methods outlined above may be used in any one of the processes listed below:
(a) reducing body weight;
(b) localized fat reduction;
(c) cellulite reduction;
(d) loose skin reduction;
(e) wrinkle treatment;
(f) body surface tightening;
(g) skin tightening;
(h) collagen remodelling; and
(i) deep wrinkle treatment.

It will be understood that other embodiments and examples of the invention will be readily apparent to a person skilled in the art, the scope and purview of the invention being defined in the appended claims.

The invention claimed is:

1. A system for thermal fat destruction and skin tightening in comprising: (a) an internal RF electrode comprising a handle, a cannula shaft extending from the handle and comprising a dielectric material, the shaft being insertable inside a body at a treatment area, and an electrode tip positioned on the cannula at a location distal to the handle, the electrode tip comprising a RF conductive material; (b) an external electrode comprising a RF conductive element, the element being positionable on a skin surface above the treatment area of the internal electrode and having larger conductive area than internal electrode; (c) a RF generator connected to the internal and external electrodes, the RF generator for delivering RF energy to the internal electrode at the level sufficient to destroy adipose tissue in vicinity of the electrode tip and to the external electrode at a level sufficient to heat the skin below second electrode to a sub-necrotic level.

2. A device according to claim 1, wherein the RF energy is generated in the frequency range of 0.2 MHz to 100 MHz.

3. A device according to claim 1, wherein the internal electrode is connected to the external electrode to maintain a predetermined distance between the electrode tip of the internal electrode and the conductive element of the external electrode.

4. A device according to claim 1 further comprising a spring mechanism acting between the internal and external electrodes to urge the electrode tip of the internal electrode to contact the conductive element of the external electrode.

5. A device for thermal fat destruction and skin tightening in comprising: (a) an internal RF electrode comprising a handle, a cannula shaft extending from the handle and comprising a dielectric material, the shaft being insertable inside a body at a treatment area, and an electrode tip positioned on the cannula at a location distal to the handle, the electrode tip comprising a RF conductive material; (b) an external electrode comprising a RF conductive element, the element being positionable on a skin surface above the treatment area of the internal electrode and having a fractional structure comprising a plurality of conductive sub-elements, the skin contact dimensions of each measure up to 1 mm; (c) a RF generator connected to the internal and external electrodes, the RF generator for delivering RF energy to the internal electrode at the level sufficient to destroy adipose tissue in vicinity of the electrode tip and to the external electrode at a level sufficient to create coagulation zones on the skin surface under the conductive sub-elements.

6. A device according to claim 5, wherein the skin contact surface area of each conductive sub-element is less than 0.5 $mm^2$.

7. A device according to claim 5, wherein the conductive sub-elements are needle shaped.

8. A device according to claim 5, wherein the external electrode is moveable over the skin surface.

9. A system for thermal fat destruction and skin tightening comprising: (a) at least one internal RF electrode comprising a handle, a cannula shaft extending from the handle and comprising a dielectric material, the shaft being insertable inside a body at a treatment area, and an electrode tip positioned on the cannula at a location distal to the handle, the electrode tip comprising a RF conductive material; (b) an external electrode comprising an electrode body, the electrode body being positionable on a skin surface above the treatment area of the internal electrode and having a plurality of conductive elements; (c) a RF generator connected to the internal and external electrodes, the RF generator for delivering RF energy to the internal electrode at the level sufficient to destroy adipose tissue in vicinity of the electrode tip and to the external electrode at a level sufficient to sufficient to heat the skin below second electrode to a sub-necrotic level; and (d) a measuring system in communication with the electrodes and the RF generator for monitoring at least one electrical parameter of RF energy for each conductive element selected from the group consisting of current, voltage and impedance.

10. A device according to claim 9 wherein the conductive elements are electrically insulated.

11. A device according to claim 9 wherein the conductive elements are grounded.

12. A device according to claim 9 wherein the measurements of electrical parameters are used for monitoring skin heating.

13. A method for thermal fat destruction and skin tightening comprising the steps: (a) inserting an internal RF electrode into adipose tissue under the skin surface; (b) positioning an external RF electrode on the skin surface above the first electrode; and (c) applying RF voltage to the electrodes sufficient to create thermal destruction of adipose tissue in vicinity of the internal electrode and sufficient to heat the skin up to sub-necrotic temperature in vicinity of external electrode.

* * * * *